US006982363B1

(12) United States Patent
Famodu et al.

(10) Patent No.: US 6,982,363 B1
(45) Date of Patent: Jan. 3, 2006

(54) UDP-GLUCOSE MODIFIERS

(75) Inventors: Omolayo O. Famodu, Newark, DE (US); Richard W. Pearlstein, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/913,060

(22) PCT Filed: Feb. 9, 2000

(86) PCT No.: PCT/US00/03513

§ 371 (c)(1),
(2), (4) Date: Aug. 8, 2001

(87) PCT Pub. No.: WO00/47748

PCT Pub. Date: Aug. 17, 2000

Related U.S. Application Data

(60) Provisional application No. 60/119,588, filed on Feb. 10, 1999.

(51) Int. Cl.
*A01H 1/00* (2006.01)
*C07H 21/04* (2006.01)
*C07K 14/415* (2006.01)
*C12N 5/14* (2006.01)
*C12N 9/00* (2006.01)

(52) U.S. Cl. .......................... 800/295; 435/6; 435/69.1; 435/468; 435/419; 435/252.3; 435/183; 435/320.1; 530/370; 536/23.6; 800/278

(58) Field of Classification Search .................. 435/6, 435/69.1, 468, 419, 252.3, 183, 320.1; 530/370; 536/23.6; 800/278, 295
See application file for complete search history.

(56) References Cited

U.S. PATENT DOCUMENTS

| 4,956,282 A | * | 9/1990 | Goodman et al. ....... 435/69.51 |
| 5,646,023 A | | 7/1997 | Secor et al. |
| 5,846,784 A | | 12/1998 | Hitz |

FOREIGN PATENT DOCUMENTS

JP          07-327679       * 12/1995

OTHER PUBLICATIONS

Kiyozumi et al., Molecular Cloning and Nucleotide Sequencing of a cDNA Encoding UDP–Glucose Pyrophosporylase of Japanese pear (Pyrus pyrifolia Naka)(Accession No. AB013353), Plant Gene Register.
Joseph R. Sowokinos et. al., Plant Phys. vol. 113:511–517, 1997, Pyrophosphorylases in Potato.
Joachim Kopka et. al., Plant J., vol. 11:871–882, 1997, Potato Guard Cells Respond to Drying Soil by a Complex Change in the Expression of Genes Related to Carbon Metabolism and Turgor Regulation.

National Center for Biotechnology Information General Indentifier No.:2117937, Jun. 16, 2000, Eimert, K et. al., Cloning and Characterization of Several cDNAs for UDP–Glucose Pyrophosphorlases From Barley (Hordeum Vulgare) Tissues.
National Center for Biotechnology Information General Indentifier No.: 322794, Jun. 18, 1999, Nakano, K., et al, UDP–Glucose Pyrophosphorylase From Potato Tober: Purification and Characterization.
Kenichi Nakano et. al., J. Biochem 106, 528–532, 1989, UDP–Glucose Pyrophosphorylases From Potato Tuber: Purification ANF Characterization.
National Center for Biotechnology Information General Identifier No.: 6136111, Jul. 15, 1999, Eimert, K., et al, Cloning and Characterization of Several cDNAs for UDP–Glucose Pyrophosphorylase From Barley (Hordeum Vulgare) Tissues.
National Center for Biotechnology Information General Identifier No.: 6136112, Aug. 20, 2001, Kiyozumi, D., et. al., Molecular Cloning and Nucleotide Sequencing of a cDNA Encoding UDP–Glucose Pyrophosporylase of Japanese Pear (Pyrus Pyrifolia Nakai).
Ted. M. Klein et. al., Nature vol. 327:70–73, 1987, High–Velocity Microprojectiles for Delivering Nucleic Acids into Living Cells.
Thomas Sims et al., Nucleic Acid Research, vol. 17(11):4388, 1989, The Glycinn GY1 Gene From Soybean.
EMBL Sequence Data Library Accession No.: AI396294, Feb. 8, 1999, Walbot, V., Maize ESTs From Various cDNA Libraries Sequenced at Standford University.
Takuya Katsube et al., Biochemistry, vol. 30:8546–8551, 1991, Expression in *Escherichia coli* of UDP–Glucose Pyrophosporylase CDNA From Potato Tuber and Functional Assessment of the Five Lysyl Residues Located at the Substrate–Binding Site.
Klaus Eimert et. al., Gene. vol. 170:227–232, 1996, Cloning and Characterization of Several cDNAs for UDP–Glucose Pyrophosphorylase From Barley (Hordeum Vulgare) Tissues.
Derwent Publications LTD., AN 1996–072337, Jun. 6, 1994, DNA Sequence Encoding Cotton UDP Glucose Synthase.

(Continued)

*Primary Examiner*—Phuong T. Bui
(74) *Attorney, Agent, or Firm*—Cozen O'Connor, P.C.; Gwilym J. O. Attwell; Lori Y. Beardell

(57) ABSTRACT

This invention relates to an isolated nucleic acid fragment encoding a UDP glucose pyrophosphorylase. The invention also relates to the construction of a chimeric gene encoding all or a portion of the UDP glucose pyrophosphorylase, in sense or antisense orientation, wherein expression of the chimeric gene results in production of altered levels of the UDP glucose pyrophosphorylase in a transformed host cell.

11 Claims, 2 Drawing Sheets

OTHER PUBLICATIONS

J. L. Ozbun et al. Plant Phys., vol. 51:1–5, 1973, Starch Synthetase Phosphorylase, Adpgluscose Pyrophosphorylase, and Udpglucose Pyrophosporylase in Developing Maize Kernels.

EMBL Sequence Data Library Accession No. AI670555, May 18, 1999, Walbot, V., Maize ESTs From Various cDNA Libraries Sequenced at Stanford University.

Kiyozumi et al., Molecular Cloning and Nucleotide Sequencing of a cDNA Encoding UDP–Glucose Pyrophosphorylase of Japanese pear (Pyrus pyrifolia Naka) (Accession No. AB013353), Plant Gene Register.

Katsube et al., "Expression in Escherichia coli of UDP–Glucose Pyrophosphorylase cDNA from Potato Tuber and Functional Assesssment of the Five Lysyl Residues Located at the Substrate–Binding Site", Biochemistry 1991, 30, 8546–8551.

Konishi et al., "Molecular Cloning, Nucleotide Sequencing, and Affinity Labeling of Bovine Liver UDP–Glucose Pyrophosphorylase", J. Biochem 114, 61–68 (1993).

Flores–Diaz et al., "Cellular UDP–Glucose Deficiency Caused by a Single Point Mutation in the UDP–Glucose Pyrophosphorylase Gene", J. Biol. Chem. 272:23784–23791 (1997).

* cited by examiner

Figure 1A

```
                  *    *      *    *      ******  *  ***  *******   *****  *****
SEQ ID NO:13      MAAAAVAADS-KIDGLRDAVAKLGEISENEKAGFISLVSRYLSGEAEQIEWSKIQTPTDE
SEQ ID NO:02      MAATAVSVDE-KLDKLRAEVAKLSQISENEKAGFISLVSRYLSGEAEQIEWSKIQTPTDE
SEQ ID NO:10      HEATLSPADADKLSNLKSSVAALSQISENEKNGFTSLVARYLSGEAQHVEWSKIETPTDE
SEQ ID NO:12      MAAAAVAADS-KIDGLRDAVAKLGISENEKAGFISLVSRYLSGEAEQIEWSKIQTPTDE
                  1                                                          60

*******  *  *  *       *                       *    *******
SEQ ID NO:13      VVVPYDTLAPPPEDLDAMKALLDKLVVLKLNGGLGTTMGCTGPKSVIEVRNGFTFLDLIV
SEQ ID NO:02      VVVPYDTLTSPPEDLEETKKLLDKLVVLKLNGGLGTTMGCTGPKSVIEVRNGFTFLDLIV
SEQ ID NO:12      VVVPYDTLAPPPEDLDAMKALLDKLVVLKLNGGLGTTMGCTGPKSVIEVRNGFTFLDLIV
SEQ ID NO:10      VVVPYDSLAPTPDGSLEVKNLLDKLVVLKLNGGLGTTMGCTGPKSVIEVRDGLTFLDLIV
                  61                                                         120

***  **  ****          *                  **            ****
SEQ ID NO:13      IQIESLNKKYGCSVPLLMNSFNTHDDTQKIVEKYSNSNIEIHTFNQSQYPRIVTEDFLP
SEQ ID NO:02      IQIESLNKKYGCNVPLLLMNSFNTHDDTQKIVEKYSNSNIEIHTFNQSQYPRIVTEDFLP
SEQ ID NO:12      IQIESLNKKYGCSVPLLMNSFNTHDDTQKIVEKYSNSNIEIHTFNQSQYPRIVTEDFLP
SEQ ID NO:10      VQIENLNSKYGSNVPLLMNSFNTHDDTQKIVEKYKNSNIEIHTFNQSQYPRLVDDFLP
                  121                                                        180

****   ****************     **  ****       ** *************
SEQ ID NO:13      LPSKGQTGKDGWYPPGHGDVFPSLNNSGKLDTLLSQGKEYVFVANSDNLGAIVDIKILNH
SEQ ID NO:02      LPSKGKSGKDGWYPPGHGDVFPSLNNSGKLDILLAQGKEYVFVANSDNLGAIVDIKILNH
SEQ ID NO:12      LPSKGQTGKDGWYPPGHGDVFPSLNNSGKLDTLLSQGKEYVFVANSDNLGAIVDIKILNH
SEQ ID NO:10      FPSKGQTGRDGWYPPGHGDVFPSLVNSGKLDVLLSQGKEYVFVANSDNLGAVVDLKILNH
                  181                                                        240
```

Figure 1B

```
              **        **********************************  **********
SEQ ID NO:13            LIHNQNEYCMEVTPKTLADVKGGTLISYEGRVQLLEIAQVPDEHVDEFKSIEKFKIFNTN
SEQ ID NO:02            LINNQNEYCMEVTPKTLADVKGGTLISYEGRVQLLEIAQVPDEHVNEFKSIEKFKIFNTN
SEQ ID NO:12            LITNQNEYCMEVTPKTLADVKGGTLISYEGRVQLLEIAQVPDEHVNEFKSIEKFKIFNTN
SEQ ID NO:10            LIEHKNEYCMEVTPKTLADVKGGTLISYEGRVQLLEIAQVPDEHVSEFKSIEKFKIFNTN
                      241                                                           300

*********  *  * ***********  **************  ************
SEQ ID NO:13  NLWVNLKAIKRLVDAEALKMEIIPNPKEVDGVKVLQLETAAGAAIRFFEKAIGINVPRSR
SEQ ID NO:02  NLWVNLKAVKRLVEAEALKMEIIPNPKEVDGVKVLQLETAAGAAIRFFDKAIGINVPRSR
SEQ ID NO:12  NLWVNLKAIKRLVDAEALKMEIIPNPKEVDGVKVLQLETAAGAAIRFFEKAIGINVPRSR
SEQ ID NO:10  NLWVNLKAIKRLVEADALKMEIIPNPKEVDGVKVLQLETAAGAAIRFFDKAIGINVPRSR
              301                                                           360

**********  ** ****  **  **************** ************
SEQ ID NO:13  FLPVKATSDLLLVQSDLYTLVDGYVIRNPARVKPSNPSIELGPEFKKVANFLARFKSIPS
SEQ ID NO:02  FLPVKATSDLLLVQSDLYTLVDGYVIRNPARVKPSNPSIELGPEFKKVANELARFKSIPS
SEQ ID NO:12  FLPVKATSDLLLVQSDLYTLVDGFVIRNPARVKPSNPSIELGPEFKKVANELARFKTIPS
SEQ ID NO:10  FLPVKATSDLLLVQSDLYTLQDGLVIRNQARANPENPSIELGPEFKKVSNFLSRFKSIPS
                                                                            420

**********  ***  ****  ** ***** ******  ******
SEQ ID NO:13  IVELDSLKVSGDVSFGSGVVLKGNVTIAAKAGVKLEIPDGAVLENKDINGPEDI
SEQ ID NO:02  IVELDSLKVSGDVWFGSGITLKGKVTITAKSGVKLEIPDGAVFENKDVNGPEDL
SEQ ID NO:12  IVELDSLKVSGDVSFGSGVVLEGNVTIAAKAGVKLEIPDGAVLENKDINGPEDL
SEQ ID NO:10  IVELDSLKVAGDVWFGAGVILKGKASILAKPGVKLEIPDGAVIADKEINGPEDL
              421                                                    474
```

UDP-GLUCOSE MODIFIERS

This application claims the benefit of U.S. Provisional Application No. 60/119,588, filed Feb. 10, 1999.

FIELD OF THE INVENTION

This invention is in the field of plant molecular biology. More specifically, this invention pertains to nucleic acid fragments encoding UDP-glucose modifiers in plants and seeds.

BACKGROUND OF THE INVENTION

UDP glucose pyrophosphorylase (EC 2.7.7.9) is also called UTP-glucose-1-phosphate uridylyltransferase or glucose-1-phosphate uridylyltransferase. It catalyzes the interconversion of G-1-P and UDP-Glucose important in starch, pectin, and hemicellulose biosynthesis. UDP glucose pyrophosphorylasecatalyzes a phosphoanhydride exchange reaction in which the phosphoryl oxygen from glucose 1-phosphate attacks the alpha phosphorus atom from UTP to form UDP glucose and release pyrophosphate which is rapidly hydrolyzed. At least two mRNA populations of UDP-glucose pyrophosphorylase are present in most European potato cultivars. These isozymes are highly active and appear to be dimeric in nature. The two cDNA populations are related to a potato cultivar's ability to resist sweetening when exposed to cold temperatures (Sowokinos et al. (1997) *Plant Physiol.* 113:511–517). UDP-glucose pyrophosphorylase mRNA levels are reduced in response to "long term" stomatal opening and closing responses to environmental stress caused in planta by withholding water over a period of 2–4 days (Kopka et al. (1997) *Plant J.* 11:871–882).

SUMMARY OF THE INVENTION

The present invention relates to isolated polynucleotides comprising a nucleotide sequence encoding a polypeptide of at least 100 amino acids that has at least 100% identity based on the Clustal method of alignment when compared to a UDP glucose pyrophosphorylase polypeptide selected from the group consisting SEQ ID NOs:2, 4, 6, 8, 10, and 12. The present invention also relates to an isolated polynucleotide comprising the complement of the nucleotide sequences described above.

It is preferred that the isolated polynucleotide of the claimed invention consists of a nucleic acid sequence selected from the group consisting of SEQ ID NOs:1, 3, 5, 7, 9, and 11 that codes for the polypeptide selected from the group consisting of SEQ ID NOs:2, 4, 6, 8, 10, and 12. The present invention also relates to an isolated polynucleotide comprising a nucleotide sequences of at least one of 60 (preferably at least one of 40, most preferably at least one of 30) contiguous nucleotides derived from a nucleotide sequence selected from the group consisting of SEQ ID NOs:1, 3, 5, 7, 9, and 11 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a UDP glucose pyrophosphorylase polypeptide of at least 100 amino acids comprising at least 100% homology based on the Clustal method of alignment compared to a polypeptide selected from the group consisting of SEQ ID NOs:2, 4, 6, 8, 10, and 12.

The present invention relates to a method of selecting an isolated polynucleotide that affects the level of expression of a UDP glucose pyrophosphorylase polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a UDP glucose pyrophosphorylase polypeptide in the host cell containing the isolated polynucleotide; and (d) comparing the level of a UDP glucose pyrophosphorylase polypeptide in the host cell containing the isolated polynucleotide with the level of a UDP glucose pyrophosphorylase polypeptide in the host cell that does not contain the isolated polynucleotide.

The present invention relates to a method of obtaining a nucleic acid fragment encoding a substantial portion of a UDP glucose pyrophosphorylase polypeptide, preferably a plant UDP glucose pyrophosphorylase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, and 11 and the complement of such nucleotide sequences; and amplifying a nucleic acid fragment (preferably a cDNA inserted in a cloning vector) using the oligonucleotide primer. The amplified nucleic acid fragment preferably will encode a portion of a UDP glucose pyrophosphorylase amino acid sequence.

The present invention also relates to a method of obtaining a nucleic acid encoding all or a substantial portion of the amino acid sequence of a UDP glucose pyrophosphorylase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

The present invention relates to a composition, such as a hybridization mixture, comprising an isolated polynucleotide of the present invention.

The present invention relates to an isolated polynucleotide of the present invention comprising at least one of 30 contiguous nucleotides derived from a nucleic acid sequence selected from the group consisting of SEQ ID NOs:1, 3, 5, 7, 9, and 11.

The present invention relates to an expression cassette comprising an isolated polynucleotide of the present invention operably linked to a promoter.

The present invention relates to a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the UDP glucose pyrophosphorylase polynucleotide in an amount sufficient to complement a null mutant to provide a positive selection means.

BRIEF DESCRIPTION OF THE DRAWING AND SEQUENCE DESCRIPTIONS

The invention can be more fully understood from the following detailed description and the accompanying drawing and Sequence Listing which form a part of this application.

FIGS. 1A and 1B depict the amino acid sequence alignment between the UDP glucose pyrophosphorylase from corn (clone p0006.cbyvq06rb; SEQ ID NO:2), soybean (clone sdp3c.pk013.121; SEQ ID NO:10), wheat (clone w1e1n.pk0063.d7; SEQ ID NO:12) and Hordeum vulgare (NCBI General Identifier No. 2117937 or 6136111; SEQ ID NO:13). Amino acids which are conserved among all sequences are indicated with an asterisk (*) above the alignment. Dashes are used by the program to maximize the alignment.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

UDP Glucose Pyrophosphorylase

| | | SEQ ID NO: | |
|---|---|---|---|
| Plant | Clone Designation | (Nucleotide) | (Amino Acid) |
| Corn | p0006.cbyvq06rb | 1 | 2 |
| Soybean | sdp3c.pk013.121 | 3 | 4 |
| Wheat | Contig of:<br>wdk1c.pk006.a12<br>w1e1n.pk0063.d7 | 5 | 6 |
| Rice | r1s6.pk0086.b8 | 7 | 8 |
| Soybean | sdp3c.pk013.121:fis | 9 | 10 |
| Wheat | w1e1n.pk0063.d7:fis | 11 | 12 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, and 11, or the complement of such sequences.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 30 (preferably at least one of 40, most preferably at least one of 60) contiguous nucleotides derived from a nucleotide sequence selected from the group consisting of SEQ ID NOs:1, 3, 5, 7, 9, and 11 and the complement of such nucleotide sequences may be used in methods of selecting an isolated UDP glucose pyrophosphorylase polynucleotide that affects the expression of a UDP glucose pyrophosphorylase polypeptide in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic orgarismns that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "tansgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several UDP-glucose modifying enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other UDP glucose pyrophosphorylases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, and 11 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a UDP glucose pyrophosphorylase polypeptide preferably a substantial portion of a plant UDP glucose pyrophosphorylase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9, and 11, and the complement of such nucleotide sequences; and amplifying a nucleic acid fragment (preferably a cDNA inserted in a cloning vector) using the oligonucleotide primer. The amplified nucleic acid fragment preferably will encode a portion of a UDP glucose pyrophosphorylase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polygonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of cell wall and starch biosynthesis in those cells. Modulation of the expression of UDP-glucose pyrophosphorylase can be used to control carbohydrate partitioning between cell wall and starch biosynthesis. Suppression of this enzyme, for example, would be expected to shift carbon flux from the cell wall pathways using UDPG toward starch biosynthesis using G-1-P.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptide (or portions thereof) may be produced in heterologous host cells, particularly in the cells of microbial hosts, and can be used to prepare antibodies to the these proteins by methods well known to those skilled in the art. The antibodies are useful for detecting the polypeptide of the instant invention in situ in cells or in vitro in cell extracts. Preferred heterologous host cells for production of the instant polypeptide are microbial hosts. Microbial expression systems and expression vectors containing regulatory sequences that direct high level expression of foreign proteins are well known to those skilled in the art. Any of these could be used to construct a chimeric gene for production of the instant polypeptide. This chimeric gene could then be introduced into appropriate microorganisms via transformation to provide high level expression of the encoded UDP glucose pyrophosphorylase. An example of a vector for high level expression of the instant polypeptide in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific. DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptide disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
| --- | --- | --- |
| p0006 | Corn Young Shoot | p0006.cbyvq06rb |
| rls6 | Rice Leaf 15 Days After Germination, 6 Hours After Infection of Strain *Magaporthe grisea* 4360-R-67 (AVR2-YAMO); Susceptible | rls6.pk0086.b8 |
| sdp3c | Soybean Developing Pods (8–9 mm) | sdp3c.pk013.121 |
| wdk1c | Wheat Developing Kernel, 3 Days After Anthesis | wdk1c.pk006.a12 |
| wle1n | Wheat Leaf From 7 Day Old Etiolated Seedling* | wle1n.pk0063.d7 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding UDP-glucose modifying enzymes were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding UDP Glucose Pyrophosphorylase

The BLASTX search using the EST sequences from clones listed in Table 3 revealed similarity of the polypeptides encoded by the cDNAs to UDP glucose pyrophosphorylase from *Hordeum vulgare* and *Solanum tuberosum* (NCBI General Identifier Nos. 2117937 and 322794, respectively). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to UDP Glucose Pyrophosphorylase

| | | BLAST pLog Score | |
|---|---|---|---|
| Clone | Status | 2117937 | 322794 |
| p0006.cbyvq06rb | CGS | >254 | >254 |
| sdp3c.pk013.121 | EST | 76.00 | 83.00 |
| Contig of wdk1c.pk006.a12 wle1n.pk0063.d7 | Contig | 102.00 | 74.52 |

The sequence of the entire cDNA insert in clones sdp3c.pk0131.121 and wle1n.pk0063.d7 was determined and further searching of the DuPont proprietary database allowed the identification of a rice clone encoding UDP glucose pyrophosphorylase. The BLAST search using the sequences from clones listed in Table 4 revealed similarity of the polypeptides encoded by the cDNAs to UDP glucose pyrophosphorylase from *Hordeum vulgare* and *Pyrus pyrifolia* (NCBI General Identifier Nos. 6136111 and 6136112, respectively). The amino acid sequence of the *Hordeum vulgare* UDP glucose pyrophosphorylase found in NCBI General Identifier No. 6136111 is 100% identical to the amino acid sequence of the *Hordeum vulgare* UDP glucose pyrophosphorylase found in NCBI General Identifier No. 2117937. Shown in Table 4 are the BLAST results for individual ESTs ("EST"), or the sequences of the entire cDNA inserts comprising the indicated cDNA clones and encoding the entire protein ("CGS"):

TABLE 4

BLAST Results for Sequences Encoding Polypeptides Homologous to UDP Glucose Pyrophosphorylase

| Clone | Status | NCBI General Identifier No. | BLAST pLog Score |
|---|---|---|---|
| r1s6.pk0086.b8 | EST | 6136111 | 67.15 |
| sdp3c.pk013.121:fis | CGS | 6136112 | >254.00 |
| wlc1n.pk0063.d7:fis | CGS | 6136111 | >254.00 |

FIG. 1 presents an alignment of the amino acid sequences set forth in SEQ ID NOs:2, 10, and 12 and the *Hordeum vulgare* sequence (SEQ ID NO:13). The data in Table 5 represents a calculation of the percent identity of the amino acid sequences set forth in SEQ ID NOs:2, 4 6, 8, 10, and 12 and the *Hordeum vulgare* sequence (SEQ ID NO:13).

TABLE 5

Percent Identity of Amino Acid Sequences Deduced From the Nucleotide Sequences of cDNA Clones Encoding Polypeptides Homologous to UDP Glucose Pyrophosphorylase

| SEQ ID NO. | Percent Identity to 6136111 or 2117937 |
|---|---|
| 2 | 91.3 |
| 4 | 75.8 |
| 6 | 96.6 |
| 8 | 70.7 |
| 10 | 83.3 |
| 12 | 98.9 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire corn, soybean, and wheat UDP glucose pyrophosphorylase and a substantial portion of rice, soybean, and wheat UDP glucose pyrophosphorylase. These sequences represent the first corn, rice, soybean, and wheat sequences encoding UDP glucose pyrophosphorylase.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR The amplified DNA is then digested with restriction enzymes NcoI and SmaI and fractionated on an agarose gel. The appropriate band can be isolated from the gel and combined with a 4.9 kb NcoI-SmaI fragment of the Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform E. coli XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptide in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptide can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 $\mu$g/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 $\mu$L of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 $\mu$g/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-$\beta$-galactoside, the inducer) can be added to a final concentration of 0.4 mM and incubation can be continued for 3 h at 25°. Cells are then harvested by centrifugation and re-suspended in 50 $\mu$L of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One $\mu$g of protein from the soluble fraction of the culture can be separated by SDS-polyacrylamide gel electrophoresis. Gels can be observed for protein bands migrating at the expected molecular weight.

Example 7

Functional Expression of the Soybean UDP-Galactose 4-Epimerase in Soybean Somatic Embryos The ability to change the levels of the raffinosaccharide pathway by overexpressing the gene from soybean clone s1s2c.pk017.k22:fis in soybean somatic embryos was tested by preparing transgenic soybean somatic embryos and assaying the raffinose, stachyose, and sucrose levels. A cosuppressed phenotype should have low to nondetectable levels of raffinose and stachyose and increased levels of sucrose and can be expressed as a ratio of sucrose/(raffinose+stachyose). A ratio of less than 1 is considered a wild type phenotype, while a ratio of greater than 2.0 is considered a cosuppressed event.

The entire insert from clone s1s2c.pk017.k22:fis was amplified in a standard PCR reaction on a Perkin Elmer Applied Biosystems GeneAmp PCR System using Pfu polymerase (Stratagene). The resulting fragment is bound by an Nco I site at the 5' end and by a Pst I fragment at the 3' end. This fragment was digested, isolated, and ligated into the Nco I/Pst I sites of plasmid pKS18HH (described in U.S. Pat. No. 5,846,784) which had been modified by the insertion of the soybean glycinin subunit G1 promoter and terminator signals at the Sac I site. The sequence of the soybean Gy1 glycinin subunit G1 was published by Sims and Goldberg (1989, Nucl. Acids Res. 17:4386). The promoter sequence consists of nucleotides 1 through 690 and the terminator sequence consists of nucleotides 3126 through 3527. The new plasmid was named G1-epimerase and contains the Gy1 promoter, the epimerase sequence, and the Gy1 termination signal surrounded by Sac I sites in plasmid pKS18HH.

Transformation of Soybean Somatic Embryo Cultures

The following stock solutions and media were used for transformation and propagation of soybean somatic embryos:

| Stock Solutions | | Media |
|---|---|---|
| MS Sulfate 100× stock | (g/L) | SB55 (per Liter) |
| $MgSO_4.7H_2O$ | 37.0 | 10 mL of each MS stock |
| $MnSO_4.H_2O$ | 1.69 | 1 mL of B5 Vitamin stock |
| $ZnSO_4.7H_2O$ | 0.86 | 0.8 g $NH_4NO_3$ |
| $CuSO_4.5H_2O$ | 0.0025 | 3.033 g $KNO_3$ |
| | | 1 mL 2,4-D (10 mg/mL stock) |
| MS Halides 100× stock | | 0.667 g asparagine |
| $CaCl_2.2H_2O$ | 44.0 | pH 5.7 |
| KI | 0.083 | |
| $COCl_2.6H_2O$ | 0.00125 | SB103 (per Liter) |
| $KH_2PO_4$ | 17.0 | 1 pk. Murashige & Skoog salt mixture* |
| $H_3BO_3$ | 0.62 | 60 g maltose |
| $Na_2MoO_4.2H_2O$ | 0.025 | 2 g gelrite |
| $Na_2EDTA$ | 3.724 | pH 5.7 |
| $FeSO_4.7H_2O$ | 2.784 | |
| | | SB148 (per Liter) |
| B5 Vitamin stock | | 1 pk. Murashige & Skoog salt mixture* |
| myo-inositol | 100.0 | 60 g maltose |
| nicotinic acid | 1.0 | 1 mL B5 vitamin stock |
| pyridoxine HCl | 1.0 | 7 g agarose |
| thiamine | 10.0 | pH 5.7 |

*(Gibco BRL)

Soybean embryonic suspension cultures were maintained in 35 mL liquid media (SB55) on a rotary shaker (150 rpm) at 28° C. with a mix of fluorescent and incandescent lights providing a 16 h day 8 h night cycle. Cultures were subcultured every 2 to 3 weeks by inoculating approximately 35 mg of tissue into 35 mL of fresh liquid media.

Soybean embryonic suspension cultures were transformed with G1-epimerase by the method of particle gun bombardment (see Klein et al. (1987) Nature 327:70–73) using a DuPont Biolistic PDS1000/He instrument. Five µL of G1-epimerase plasmid DNA (1 g/L), 50 µL $CaCl_2$ (2.5 M), and 20 µL spermidine (0.1 M) were added to 50 µl of a 60 mg/mL 1 mm gold particle suspension. The particle preparation was agitated for 3 minutes, spun in a microfuge for 10 seconds and the supernate removed. The DNA-coated particles were then washed once with 400 µL of 70% ethanol and resuspended in 40 µL of anhydrous ethanol. The DNA/particle suspension was sonicated three times for 1 second each. Five µL of the DNA-coated gold particles were then loaded on each macro carrier disk.

Approximately 300 to 400 mg of two-week-old suspension culture was placed in an empty 60 mm×15 mm petri dish and the residual liquid removed from the tissue using a pipette. The tissue was placed about 3.5 inches away from the retaining screen and bombarded twice. Membrane rupture pressure was set at 1100 psi and the chamber was evacuated to −28 inches of Hg. Two plates were bombarded, and following bombardment, the tissue was divided in half, placed back into liquid media, and cultured as described above.

Fifteen days after bombardment, the liquid media was exchanged with fresh SB55 containing 50 mg/mL hygromycin. The selective media was refreshed weekly. Six weeks after bombardment, green, transformed tissue was isolated and inoculated into flasks to generate new transformed embryonic suspension cultures.

Transformed embryonic clusters were removed from liquid culture media and placed on a solid agar media, SB103, containing 0.5% charcoal to begin maturation. After 1 week, embryos were transferred to SB103 media minus charcoal. After 5 weeks on SB103 media, maturing embryos were separated and placed onto SB148 media. During maturation embryos were kept at 26° C. with a mix of fluorescent and incandescent lights providing a 16 h day 8 h night cycle. To mimic seed dry down, embryos were harvested after 5 weeks on SB148 media. Each embryonic cluster gave rise to 5 to 20 somatic embryos.

Non-transformed somatic embryos were cultured by the same method as used for the transformed somatic embryos.

Analysis of Transformed Somatic Embryos

At the end of the $5^{th}$ week on SB148 medium somatic embryos were harvested from 14 independently transformed lines. Soluble carbohydrates were extracted by crushing the embryos with a nylon pestle in a microfuge tube containing 200 µL of 80% methanol. Extraction was repeated with an additional 200 µL of 80% methanol and the supernatants combined and dried. The soluble carbohydrates were resuspended in 200 µL water and analyzed using a Dionex DX500 chromatography system. Carbohydrates were separated on a Dionex CarboPac PAI (4×250 mm) column using 95% 0.2 M NaOH, 5% water at 1.0 ml/min. A total of 14 events (10 embryos each) were analyzed. The total area for the sugars raffinose, stachyose and sucrose were tabulated for each embryo. A cosuppressed phenotype should have low to nondetectable levels of raffinose and stachyose and increased levels of sucrose and can be expressed as a ratio of sucrose/(raffinose+stachyose). A ratio of less than 1.0 is considered a wildtype phenotype, while a ratio of greater than 2.0 is considered a cosuppressed event. The averages and standard deviations for the areas of sucrose, raffinose, stachyose, and the ratio of sucrose/(raffinose+stachyose) for each of the 14 samples are indicated in Table 6:

TABLE 6

Averages and Standard Deviations of the Carbohydrates From Somatic Soybean Embryos Expressing Chimeric Soybean UDP-Galactose 4-Epimerases

| Somatic Embryo | Sucrose | Raffinose | Stachyose | Sucrose/(Raffinose + Stachyose) |
|---|---|---|---|---|
| 4/4 | 3568973.7 ± 1408264.7 | 1045112.8 ± 641756.9 | 3967517 ± 2900645.5 | 1.02 ± 0.8 |
| 4/5 | 2856327.7 ± 707852.7 | 904544 ± 521259.0 | 3557979.3 ± 1715496.3 | 0.88 ± 0.7 |
| 4/7 | 2877070.1 ± 873920.3 | 717643.3 ± 609431.0 | 3009836.7 ± 2407257.1 | 1 ± 0.4 |
| 4/1 | 2653179.9 ± 1046953.1 | 709370 ± 379902.4 | 3876536.5 ± 1999692.2 | 0.77 ± 0.5 |
| 4/2 | 2857092.7 ± 742415.0 | 626307.5 ± 115743.8 | 3121925.9 ± 951294.5 | 0.76 ± 0.08 |
| 4/6 | 3112203.2 ± 850601.7 | 754341.9 ± 262408.2 | 4601053 ± 1461924.7 | 0.61 ± 0.15 |
| 4/3 | 3282564.1 ± 1911513.1 | 706353.5 ± 428861.1 | 4602803.6 ± 2261654.1 | 0.58 ± 0.17 |
| 3/3 | 2691493.3 ± 1538378.2 | 536062.6 ± 231855.5 | 2838255.8 ± 1048200.9 | 0.77 ± 0.32 |
| 3/1 | 2283160.5 ± 1089482.4 | 449773.1 ± 229549.7 | 1983356 ± 1099495.3 | 1.44 ± 1.25 |
| 3/4 | 3375314.6 ± 1805313.2 | 616473.8 ± 185309.4 | 3940545.5 ± 845544.6 | 0.76 ± 0.19 |
| 3/6 | 81106208.1 ± 30013245.6 | 17813664.4 ± 9546497.2 | 101268706.9 ± 50277358.9 | 0.72 ± 0.14 |
| 3/2 | 89847214.2 ± 14908804.2 | 17040544.3 ± 5550687.9 | 88496699.5 ± 34107697.8 | 1.05 ± 0.70 |
| 3/1 (repeat) | 73558780.2 ± 35218563.3 | 17948085.3 ± 14008680.2 | 73769338.2 ± 49942666.1 | 1.46 ± 1.51 |
| 3/5 | 68427093.9 ± 20712691.0 | 13192646.4 ± 9066329.2 | 55486977 ± 36156784.6 | 1.24 ± 0.75 |

Of the 14 events analyzed, two were considered cosuppressed for UDP-glucose 4'epimerase (4/1 and 3/1). Both of these events have at least 2 embryos that have a ratio greater than 2.0. Event 3/1 was repeated and both times exhibited cosuppression.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated nucleic acid comprising a polynucleotide consisting of:
   (a) a nucleotide sequence encoding a polypeptide having UDP-glucose pyrophosphorylase activity, wherein the polypeptide has an amino acid sequence of at least 90% sequence identity, based on the Clustal V method of alignment, when compared to SEQ ID NO:10, or
   (b) a full-length complement of the nucleotide sequence of (a).

2. The polynucleotide of claim 1, wherein the amino add sequence of the polypeptide has at least 95% sequence identity, based on the Clustal V method of alignment, when compared to SEQ ID NO:10.

3. The polynucleotide of claim 1, wherein the amino acid sequence of the polypeptide comprises SEQ ID NO:10.

4. The polynucleotide of claim 1, wherein the nucleotide sequence comprises SEQ ID NO:9.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

SEQUENCE LISTING

<160> NUMBER OF SEQ ID NOS: 13

<210> SEQ ID NO 1
<211> LENGTH: 1960
<212> TYPE: DNA
<213> ORGANISM: Zea mays

<400> SEQUENCE: 1

```
ggcacgaggg ggaagggcgc ggcatgcgct gaagacagtc tgaggcgctg cgggcagtct      60
aacagcaccc cctcctcgct cgcactccgt tcgtctgaca tctcctcccg tcctttcctt     120
tctgaggctc gcgaacccceg acaatggccg caaccgcggt gtcggtcgac gagaagctcg     180
acaagcttcg cgccgaggtc gccaaactca gccagatcag cgagaacgag aaggccgggt     240
tcatcagcct cgtgtcacgc tacctcagtg gggaggcgga gcagatcgag tggagcaaga     300
tccagacccc gaccgatgag gtagtggtgc cgtacgatac cctcacgtcg cctcctgaag     360
atctcgagga gacgaagaag ctgctggaca agctcgttgt gctcaagctc aacggagggc     420
tcgggacgac catgggctgc accggaccca agtctgtcat tgaagtccgc aatgggttca     480
cattccttga ccttattgtg attcaaatcg agtccctgaa caagaagtat ggatgtaatg     540
tccctttact tctgatgaac tctttcaata cccatgatga cacacagaag atcgttgaga     600
agtattccaa ctccaacatt gaaattcata ctttcaatca gagccagtat cctcgcattg     660
ttaccgagga cttcttgcca cttccaagca aagggaaatc tgggaaggat ggctggtatc     720
ctccaggcca tggtgatgtg ttcccctctt tgaataacag tggaaaactc gacatcttat     780
tggctcaggg caaggagtat gtcttcgttg ctaactcaga caacttgggt gctatagtcg     840
```

-continued

```
acatcaagat cctgaaccat ctgatcaata accagaatga atactgcatg gaggttactc    900
caaaaacatt ggctgatgtt aaaggcggta ctctcatctc ttacgaagga agagttcagc    960
ttttggagat tgcccaagta cctgatgagc atgtgaatga gtttaaatca atcgagaagt   1020
ttaagatatt caacactaac aacttgtggg tgaaccttaa agctgtcaag agactagtag   1080
aggctgaggc acttaagatg gaaattattc caaaccccaa ggaagttgat ggtgtgaaag   1140
tccttcaact tgaaactgca gctggtgcag ctattcgttt ctttgacaaa gcgattggaa   1200
ttaatgttcc ccgctcaaga tttctcccgg tgaaggctac atctgattta ttgcttgtgc   1260
agtctgatct ttacaccttg gttgatggct tgtcatccg caatccatcc agagcgaatc   1320
cagctaaccc ttcgattgag cttggacctg agttcaagaa ggttgccaat ttccttgctc   1380
ggttcaagtc catccccagc atcgtcgagc ttgacagctt gaaggtttct ggtgatgtct   1440
ggtttggttc tggaattacg ctcaagggca aggtgacaat caccgccaag tctggagtga   1500
agttggaggt tccagatgga gctgtatttg aaaacaagga tgtcaatggc cctgaggatc   1560
tttaagctat gcttgccgtc accagttttt cccaaggatt tgtcaatagg agcagccaac   1620
ccaaatcact cccactgagc tctacctttt gtaattctcg tgccattccg ctcccgctgt   1680
gagggtcctg tgagcccgct agagaatatg actgtaatct tctttggtgc gtctgccctt   1740
ctgttttgt gcgccaggga cgtatatttt gctgaaatga tactaccata gctttgcgtg   1800
ccggaggtgc tatgtggtgt ttctgtgcgt ttggttgcaa tgataggacg ggatgagatg   1860
agaccctcaa attaggttgt ttggttctgg gtcaaagatt gagacaagaa tatcctagta   1920
ttgtttcatg ttgtccttta aaaaaaaaaa aaaaaaaaa                          1960
```

<210> SEQ ID NO 2
<211> LENGTH: 473
<212> TYPE: PRT
<213> ORGANISM: Zea mays

<400> SEQUENCE: 2

```
Met Ala Ala Thr Ala Val Ser Val Asp Glu Lys Leu Asp Lys Leu Arg
  1               5                  10                  15

Ala Glu Val Ala Lys Leu Ser Gln Ile Ser Glu Asn Glu Lys Ala Gly
                 20                  25                  30

Phe Ile Ser Leu Val Ser Arg Tyr Leu Ser Gly Glu Ala Glu Gln Ile
             35                  40                  45

Glu Trp Ser Lys Ile Gln Thr Pro Thr Asp Glu Val Val Pro Tyr
         50                  55                  60

Asp Thr Leu Thr Ser Pro Pro Glu Asp Leu Glu Thr Lys Lys Leu
 65                  70                  75                  80

Leu Asp Lys Leu Val Val Leu Lys Leu Asn Gly Gly Leu Gly Thr Thr
                 85                  90                  95

Met Gly Cys Thr Gly Pro Lys Ser Val Ile Glu Val Arg Asn Gly Phe
                100                 105                 110

Thr Phe Leu Asp Leu Ile Val Ile Gln Ile Glu Ser Leu Asn Lys Lys
            115                 120                 125

Tyr Gly Cys Asn Val Pro Leu Leu Leu Met Asn Ser Phe Asn Thr His
        130                 135                 140

Asp Asp Thr Gln Lys Ile Val Glu Lys Tyr Ser Asn Ser Asn Ile Glu
145                 150                 155                 160

Ile His Thr Phe Asn Gln Ser Gln Tyr Pro Arg Ile Val Thr Glu Asp
                165                 170                 175
```

```
Phe Leu Pro Leu Pro Ser Lys Gly Lys Ser Gly Lys Asp Gly Trp Tyr
            180                 185                 190
Pro Pro Gly His Gly Asp Val Phe Pro Ser Leu Asn Asn Ser Gly Lys
            195                 200                 205
Leu Asp Ile Leu Leu Ala Gln Gly Lys Glu Tyr Val Phe Val Ala Asn
    210                 215                 220
Ser Asp Asn Leu Gly Ala Ile Val Asp Ile Lys Ile Leu Asn His Leu
225                 230                 235                 240
Ile Asn Asn Gln Asn Glu Tyr Cys Met Glu Val Thr Pro Lys Thr Leu
                245                 250                 255
Ala Asp Val Lys Gly Gly Thr Leu Ile Ser Tyr Glu Gly Arg Val Gln
            260                 265                 270
Leu Leu Glu Ile Ala Gln Val Pro Asp Glu His Val Asn Glu Phe Lys
        275                 280                 285
Ser Ile Glu Lys Phe Lys Ile Phe Asn Thr Asn Asn Leu Trp Val Asn
    290                 295                 300
Leu Lys Ala Val Lys Arg Leu Val Glu Ala Glu Ala Leu Lys Met Glu
305                 310                 315                 320
Ile Ile Pro Asn Pro Lys Glu Val Asp Gly Val Lys Val Leu Gln Leu
                325                 330                 335
Glu Thr Ala Ala Gly Ala Ala Ile Arg Phe Phe Asp Lys Ala Ile Gly
            340                 345                 350
Ile Asn Val Pro Arg Ser Arg Phe Leu Pro Val Lys Ala Thr Ser Asp
        355                 360                 365
Leu Leu Leu Val Gln Ser Asp Leu Tyr Thr Leu Val Asp Gly Phe Val
    370                 375                 380
Ile Arg Asn Pro Ser Arg Ala Asn Pro Ala Asn Pro Ser Ile Glu Leu
385                 390                 395                 400
Gly Pro Glu Phe Lys Lys Val Ala Asn Phe Leu Ala Arg Phe Lys Ser
                405                 410                 415
Ile Pro Ser Ile Val Glu Leu Asp Ser Leu Lys Val Ser Gly Asp Val
            420                 425                 430
Trp Phe Gly Ser Gly Ile Thr Leu Lys Gly Lys Val Thr Ile Thr Ala
        435                 440                 445
Lys Ser Gly Val Lys Leu Glu Val Pro Asp Gly Ala Val Phe Glu Asn
    450                 455                 460
Lys Asp Val Asn Gly Pro Glu Asp Leu
465                 470
```

<210> SEQ ID NO 3
<211> LENGTH: 519
<212> TYPE: DNA
<213> ORGANISM: Glycine max
<220> FEATURE:
<221> NAME/KEY: unsure
<222> LOCATION: (188)
<223> OTHER INFORMATION: n=a,c,g or t
<220> FEATURE:
<221> NAME/KEY: unsure
<222> LOCATION: (518)
<223> OTHER INFORMATION: n=a,c,g or t

<400> SEQUENCE: 3

```
gccacgctta gccccgccga cgccgacaag ctctccaacc tcaaatcctc cgtcgctgca      60
ttgagccaaa tcagtgagaa tgagaagaat ggattcacaa gcctcgttgc tcgttacctc     120
agtggcgaag cacagcatgt tgagtggagt aagatcgaga cgcctacgga tgaagtagtg     180
```

-continued

| | |
|---|---|
| gtgccttntg actctttggc accgactcct gacggttctt tggaggtgaa gaacctcttg | 240 |
| gacaagcttg tggtgttgaa gctcaatgga ggcttgggga caactatggg ttgtactggc | 300 |
| ccaaaatctg tcattgaagt tcgtgatggg ttgacatttc ttgatttaat tgtcgtccaa | 360 |
| attgagaacc tcaattccaa atacggaagc aatgttccgt tgcttttaat gaactcattc | 420 |
| aacactcatg atgacactca aaagattgtt gagaaatata aaaactcaaa tattgagatt | 480 |
| catacgttta accaagagtc aatatcctcg tttggttng | 519 |

<210> SEQ ID NO 4
<211> LENGTH: 165
<212> TYPE: PRT
<213> ORGANISM: Glycine max
<220> FEATURE:
<221> NAME/KEY: UNSURE
<222> LOCATION: (63)
<223> OTHER INFORMATION: Xaa = ANY AMINO ACID

<400> SEQUENCE: 4

Ala Thr Leu Ser Pro Ala Asp Ala Glu Lys Leu Asn Asn Leu Lys Ser
 1               5                  10                  15

Ala Val Ala Gly Leu Asn Gln Ile Ser Asp Asn Glu Lys Ser Gly Phe
            20                  25                  30

Ile Asn Leu Val Gly Arg Tyr Leu Ser Gly Glu Ala Gln His Ile Asp
        35                  40                  45

Trp Ser Lys Ile Gln Thr Pro Thr Asp Glu Val Val Pro Xaa Asp
    50                  55                  60

Ser Leu Ala Pro Thr Pro Asp Gly Ser Leu Glu Val Lys Asn Leu Leu
65                  70                  75                  80

Asp Lys Leu Val Val Leu Lys Leu Asn Gly Gly Leu Gly Thr Thr Met
                85                  90                  95

Gly Cys Thr Gly Pro Lys Ser Val Ile Glu Val Arg Asp Gly Leu Thr
            100                 105                 110

Phe Leu Asp Leu Ile Val Val Gln Ile Glu Asn Leu Asn Ser Lys Tyr
        115                 120                 125

Gly Ser Asn Val Pro Leu Leu Leu Met Asn Ser Phe Asn Thr His Asp
    130                 135                 140

Asp Thr Gln Lys Ile Val Glu Lys Tyr Lys Asn Ser Asn Ile Glu Ile
145                 150                 155                 160

His Thr Phe Asn Gln
            165

<210> SEQ ID NO 5
<211> LENGTH: 582
<212> TYPE: DNA
<213> ORGANISM: Triticum aestivum
<220> FEATURE:
<221> NAME/KEY: unsure
<222> LOCATION: (461)
<223> OTHER INFORMATION: n=a,c,g or t
<220> FEATURE:
<221> NAME/KEY: unsure
<222> LOCATION: (582)
<223> OTHER INFORMATION: n=a,c,g or t

<400> SEQUENCE: 5

| | |
|---|---|
| gccacctctc ccttccagtc atctgacatc tgctcccgtc ctctcctcct ctcccccga | 60 |
| agcagcgtgc gcgtcgctcc tctccgcccg gatcgcgatg ccgccgccg ccgtcgccgc | 120 |
| cgactccaag atcgacggcc tccgcgacgc cgtcgccaag ctcggcgaga tcagcgagaa | 180 |

-continued

```
cgagaaggcc gggttcatca gcctcgtctc gcgctacctc agcggcgagg cggagcagat    240
cgagtggagc aagatccaga ccccaccga tgaggtggtg gtgccctacg acaccctcgc    300
gccccctccc gaagatctcg acgccatgaa ggcgctgctc gacaagctcg tggtgctcaa    360
gctcaacgga ggcctcggca ccaccatggg ctgcaccggc ccaagtctg tcattgaagt    420 tcgcaatggg gtttacattt cttgaccta atgtgattca nattgagtcc ctgaaacaag    480
aagtatggat gcagtgttcc tttgcttcta atgaactctt tcaacactca tgacgacaca    540
cagaagattt tgagaagtac tccaactcca acattgaaaa tn                      582
```

<210> SEQ ID NO 6
<211> LENGTH: 118
<212> TYPE: PRT
<213> ORGANISM: Triticum aestivum
<400> SEQUENCE: 6

```
Met Ala Ala Ala Val Ala Ala Asp Ser Lys Ile Asp Gly Leu Arg
 1               5                  10                  15

Asp Ala Val Ala Lys Leu Gly Glu Ile Ser Glu Asn Glu Lys Ala Gly
            20                  25                  30

Phe Ile Ser Leu Val Ser Arg Tyr Leu Ser Gly Glu Ala Glu Gln Ile
        35                  40                  45

Glu Trp Ser Lys Ile Gln Thr Pro Thr Asp Glu Val Val Val Pro Tyr
    50                  55                  60

Asp Thr Leu Ala Pro Pro Glu Asp Leu Asp Ala Met Lys Ala Leu
 65                  70                  75                  80

Leu Asp Lys Leu Val Val Leu Lys Leu Asn Gly Gly Leu Gly Thr Thr
                85                  90                  95

Met Gly Cys Thr Gly Pro Lys Ser Val Ile Glu Val Arg Asn Gly Leu
            100                 105                 110

His Phe Leu Thr Leu Met
        115
```

<210> SEQ ID NO 7
<211> LENGTH: 633
<212> TYPE: DNA
<213> ORGANISM: Oryza sativa
<220> FEATURE:
<221> NAME/KEY: unsure
<222> LOCATION: (480)
<223> OTHER INFORMATION: n=a,c,g or t
<220> FEATURE:
<221> NAME/KEY: unsure
<222> LOCATION: (549)
<223> OTHER INFORMATION: n=a,c,g or t
<220> FEATURE:
<221> NAME/KEY: unsure
<222> LOCATION: (553)
<223> OTHER INFORMATION: n=a,c,g or t
<220> FEATURE:
<221> NAME/KEY: unsure
<222> LOCATION: (617)..(618)
<223> OTHER INFORMATION: n=a,c,g or t
<400> SEQUENCE: 7

```
gttctaacct cctctcctct catctgacat atctcctccc gtcctttcga agcctctcga    60
atcgcatcgc cgagccggat ggcggtcacc gccgacgtga agctcgaggg cctccgcgcc   120
gccaccgaca agctcgacca gatcagcgag aacgagaagt ccgggttcat cagcctcgtt   180
tcgcgctacc tcagcggcga ggcggagcag atcgagtgga gtaagatcca gaccccgacc   240
```

```
gacgaggtgg tggttcccta cgacacgctc tcggctgctc ccgaagatct caacgagacg    300
aagaagctgc tcgacaaact cgtccgtgct caagctcaat ggaggcctcg ggacgaccat    360
gggctgcact gggtcccaag tctgtcattg aagtccgcaa tggctttacg tttctagacc    420
ttattgtgat tcaaattgat ccctgaacaa gaagtatgga tgcaatgtcc ctttgcttcn    480
aatgaactca tcaacactca tgatgacaca cagaagaatg ttgagaagta ctccaactcc    540
aacattgana tcncacttta accagagcca atatcccgca ttgttacgaa agacttcctg    600
cactcaagca aggaannat ggaaggatgg tgg                                   633
```

```
<210> SEQ ID NO 8
<211> LENGTH: 174
<212> TYPE: PRT
<213> ORGANISM: Oryza sativa
<220> FEATURE:
<221> NAME/KEY: UNSURE
<222> LOCATION: (83)
<223> OTHER INFORMATION: Xaa = ANY AMINO ACID
<220> FEATURE:
<221> NAME/KEY: UNSURE
<222> LOCATION: (123)
<223> OTHER INFORMATION: Xaa = ANY AMINO ACID
<220> FEATURE:
<221> NAME/KEY: UNSURE
<222> LOCATION: (137)
<223> OTHER INFORMATION: Xaa = ANY AMINO ACID
<220> FEATURE:
<221> NAME/KEY: UNSURE
<222> LOCATION: (141)..(142)
<223> OTHER INFORMATION: Xaa = ANY AMINO ACID
<220> FEATURE:
<221> NAME/KEY: UNSURE
<222> LOCATION: (161)
<223> OTHER INFORMATION: Xaa = ANY AMINO ACID
<220> FEATURE:
<221> NAME/KEY: UNSURE
<222> LOCATION: (163)..(164)
<223> OTHER INFORMATION: Xaa = ANY AMINO ACID

<400> SEQUENCE: 8

Met Ala Val Thr Ala Asp Val Lys Leu Glu Gly Leu Arg Ala Thr
  1               5                  10                  15

Asp Lys Leu Asp Gln Ile Ser Glu Asn Glu Lys Ser Gly Phe Ile Ser
                 20                  25                  30

Leu Val Ser Arg Tyr Leu Ser Gly Glu Ala Glu Gln Ile Glu Trp Ser
             35                  40                  45

Lys Ile Gln Thr Pro Thr Asp Glu Val Val Pro Tyr Asp Thr Leu
         50                  55                  60

Ser Ala Ala Pro Glu Asp Leu Asn Glu Thr Lys Lys Leu Leu Asp Lys
 65                  70                  75                  80

Leu Val Xaa Val Leu Lys Leu Asn Gly Gly Leu Gly Gly Arg Pro Trp
                 85                  90                  95

Ala Ala Leu Gly Pro Lys Ser Val Ile Glu Val Arg Asn Gly Phe Thr
            100                 105                 110

Phe Leu Asp Leu Ile Val Ile Gln Ile Asp Xaa Ser Leu Asn Lys Lys
        115                 120                 125

Tyr Gly Cys Asn Val Pro Leu Leu Xaa Met Asn Ser Xaa Xaa Asn Thr
    130                 135                 140

His Asp Asp Thr Gln Lys Asn Val Glu Lys Tyr Ser Asn Ser Asn Ile
145                 150                 155                 160

Xaa Ile Xaa Xaa Phe Asn Gln Ser Gln Tyr Pro Ala Leu Leu
                165                 170
```

<210> SEQ ID NO 9
<211> LENGTH: 1700
<212> TYPE: DNA
<213> ORGANISM: Glycine max

<400> SEQUENCE: 9

| | | | | | |
|---|---|---|---|---|---|
| gcacgaggcc | acgcttagcc | ccgccgacgc | cgacaagctc | tccaacctca | aatcctccgt | 60 |
| cgctgcattg | agccaaatca | gtgagaatga | gaagaatgga | ttcacaagcc | tcgttgctcg | 120 |
| ttacctcagt | ggcgaagcac | agcatgttga | gtggagtaag | atcgagacgc | tacggatga | 180 |
| agtagtggtg | ccttatgact | ctttggcacc | gactcctgac | ggttctttgg | aggtgaagaa | 240 |
| cctcttggac | aagcttgtgg | tgttgaagct | caatggaggc | ttggggacaa | ctatgggttg | 300 |
| tactggccca | aaatctgtca | ttgaagttcg | tgatggttg | acatttcttg | atttaattgt | 360 |
| cgtccaaatt | gagaacctca | attccaaata | cggaagcaat | gttccgttgc | ttttaatgaa | 420 |
| ctcattcaac | actcatgatg | acactcaaaa | gattgttgag | aaatataaaa | actcaaatat | 480 |
| tgagattcat | acgtttaacc | agagtcaata | tcctcgtttg | gttgttgatg | acttttttgcc | 540 |
| attcccatcc | aaggggcaga | caggcaggga | cgggtggtac | cctcctggcc | acggagacgt | 600 |
| cttcccatca | ttagtgaata | gtggaaagct | tgatgtgcta | ttatcacagg | gtaaggagta | 660 |
| tgtgtttgtt | gccaattcag | acaacctggg | tgctgtagtt | gacttgaaaa | tcttaaatca | 720 |
| tttgattgag | cacaagaatg | aatactgtat | ggaggtcact | cccaagacat | ggctgacgt | 780 |
| gaaaggtggc | actctgattt | cttatgaagg | aagggttcag | ctcctggaaa | ttgcccaagt | 840 |
| accagatgaa | catgtcagtg | aatttaagtc | tatagagaaa | ttcaaaattt | tcaacacaaa | 900 |
| taatttgtgg | gtaaacttga | agcaattaa | aaggcttgtt | gaagctgatg | ctctgaagat | 960 |
| ggaaattatt | cccaatccaa | aggaagtcga | tgagtaaaa | gttcttcaat | ggaaactgc | 1020 |
| agctggtgca | gcaataaggt | tctttgacaa | agctattgga | attaatgtgc | ctcgatctcg | 1080 |
| cttccttccc | gtgaaggcaa | cttcagactt | gcttcttgtc | cagtcggacc | tttacacttt | 1140 |
| acaagatgga | ttggttatta | ggaaccaagc | tagggcaaat | cctgaaaatc | cttccattga | 1200 |
| attggggcca | gaatttaaga | aggttagcaa | tttcttgagc | cggttcaagt | caatccccag | 1260 |
| tattgttgag | cttgacagtc | taaaagtggc | aggcgatgta | tggtttggag | ctggtgtaat | 1320 |
| ccttaaggga | aaagcaagta | ttcttgcaaa | accgggtgtg | aagctggaaa | tacctgacgg | 1380 |
| agctgtgatc | gcagacaagg | aaattaatgg | ccctgaggac | ctgtgagaga | aagctgatga | 1440 |
| tgagttttga | aatccatgtg | actgtgcaat | ctttgagtat | tgacagtctt | aaactaaaat | 1500 |
| ttgtgtattg | cttctagttt | ggtaggggta | aaaataagaa | ggcagtttct | actgagcatg | 1560 |
| tctgaagact | aagctttgta | tttctcataa | ttttgttttt | aaacatttct | tacaaggact | 1620 |
| caaggaggat | ccgatcatgt | ttcctttcca | tatcatatta | agcgtttacg | ccttcatctt | 1680 |
| taaaaaaaaa | aaaaaaaaa | | | | | 1700 |

<210> SEQ ID NO 10
<211> LENGTH: 474
<212> TYPE: PRT
<213> ORGANISM: Glycine max

<400> SEQUENCE: 10

His Glu Ala Thr Leu Ser Pro Ala Asp Ala Asp Lys Leu Ser Asn Leu
 1               5                  10                  15

Lys Ser Ser Val Ala Ala Leu Ser Gln Ile Ser Glu Asn Glu Lys Asn
            20                  25                  30

-continued

```
Gly Phe Thr Ser Leu Val Ala Arg Tyr Leu Ser Gly Glu Ala Gln His
             35                  40                  45

Val Glu Trp Ser Lys Ile Glu Thr Pro Thr Asp Glu Val Val Pro
     50                  55                  60

Tyr Asp Ser Leu Ala Pro Thr Pro Asp Gly Ser Leu Glu Val Lys Asn
 65                  70                  75                   80

Leu Leu Asp Lys Leu Val Val Leu Lys Leu Asn Gly Gly Leu Gly Thr
                 85                  90                  95

Thr Met Gly Cys Thr Gly Pro Lys Ser Val Ile Glu Val Arg Asp Gly
                100                 105                 110

Leu Thr Phe Leu Asp Leu Ile Val Gln Ile Glu Asn Leu Asn Ser
         115                 120                 125

Lys Tyr Gly Ser Asn Val Pro Leu Leu Met Asn Ser Phe Asn Thr
         130                 135                 140

His Asp Asp Thr Gln Lys Ile Val Glu Lys Tyr Lys Asn Ser Asn Ile
145                 150                 155                 160

Glu Ile His Thr Phe Asn Gln Ser Gln Tyr Pro Arg Leu Val Val Asp
                 165                 170                 175

Asp Phe Leu Pro Phe Pro Ser Lys Gly Gln Thr Gly Arg Asp Gly Trp
             180                 185                 190

Tyr Pro Pro Gly His Gly Asp Val Phe Pro Ser Leu Val Asn Ser Gly
             195                 200                 205

Lys Leu Asp Val Leu Leu Ser Gln Gly Lys Glu Tyr Val Phe Val Ala
         210                 215                 220

Asn Ser Asp Asn Leu Gly Ala Val Val Asp Leu Lys Ile Leu Asn His
225                 230                 235                 240

Leu Ile Glu His Lys Asn Glu Tyr Cys Met Glu Val Thr Pro Lys Thr
                 245                 250                 255

Leu Ala Asp Val Lys Gly Gly Thr Leu Ile Ser Tyr Glu Gly Arg Val
             260                 265                 270

Gln Leu Leu Glu Ile Ala Gln Val Pro Asp Glu His Val Ser Glu Phe
         275                 280                 285

Lys Ser Ile Glu Lys Phe Lys Ile Phe Asn Thr Asn Asn Leu Trp Val
         290                 295                 300

Asn Leu Lys Ala Ile Lys Arg Leu Val Glu Ala Asp Ala Leu Lys Met
305                 310                 315                 320

Glu Ile Ile Pro Asn Pro Lys Glu Val Asp Gly Val Lys Val Leu Gln
                 325                 330                 335

Leu Glu Thr Ala Ala Gly Ala Ala Ile Arg Phe Phe Asp Lys Ala Ile
             340                 345                 350

Gly Ile Asn Val Pro Arg Ser Arg Phe Leu Pro Val Lys Ala Thr Ser
             355                 360                 365

Asp Leu Leu Leu Val Gln Ser Asp Leu Tyr Thr Leu Gln Asp Gly Leu
         370                 375                 380

Val Ile Arg Asn Gln Ala Arg Ala Asn Pro Glu Asn Pro Ser Ile Glu
385                 390                 395                 400

Leu Gly Pro Glu Phe Lys Lys Val Ser Asn Phe Leu Ser Arg Phe Lys
                 405                 410                 415

Ser Ile Pro Ser Ile Val Glu Leu Asp Ser Leu Lys Val Ala Gly Asp
             420                 425                 430

Val Trp Phe Gly Ala Gly Val Ile Leu Lys Gly Lys Ala Ser Ile Leu
         435                 440                 445
```

Ala Lys Pro Gly Val Lys Leu Glu Ile Pro Asp Gly Ala Val Ile Ala
    450                 455                 460

Asp Lys Glu Ile Asn Gly Pro Glu Asp Leu
465                 470

<210> SEQ ID NO 11
<211> LENGTH: 1814
<212> TYPE: DNA
<213> ORGANISM: Triticum aestivum

<400> SEQUENCE: 11

| | | | | | |
|---|---|---|---|---|---|
| gcacgaggcc | acctctccct | tccagtcatc | tgacatctgc | tcccgtcctc | tcctcctctc | 60 |
| cccccgaagc | agcgtgcgcg | tcgctcctct | ccgcccggat | cgcgatggcc | gccgccgccg | 120 |
| tcgccgccga | ctccaagatc | gacggcctcc | gcgacgccgt | cgccaagctc | ggcgagatca | 180 |
| gcgagaacga | gaaggccggg | ttcatcagcc | tcgtctcgcg | ctacctcagc | ggcgaggcgg | 240 |
| agcagatcga | gtggagcaag | atccagaccc | ccaccgatga | ggtggtggtg | ccctacgaca | 300 |
| ccctcgcgcc | ccctcccgaa | gatctcgacg | ccatgaaggc | gctgctcgac | aagctcgtgg | 360 |
| tgctcaagct | caacggaggc | ctcggcacca | ccatgggctg | caccggcccc | aagtctgtca | 420 |
| ttgaagttcg | caatgggttt | acatttcttg | accttattgt | gattcagatt | gagtccctga | 480 |
| acaagaagta | tggatgcagt | gttcctttgc | ttctaatgaa | ctctttcaac | actcatgacg | 540 |
| acacacagaa | gattgttgag | aagtactcca | actccaacat | tgaaattcac | actttcaacc | 600 |
| agagccaata | ccctcgcatt | gttactgaag | acttcttgcc | acttccaagc | aaagggcaga | 660 |
| cagggaagga | tggctggtac | ccccaggcc | acggtgatgt | gttcccctct | ttgaacaaca | 720 |
| gtggaaaact | cgatacccttg | ctgtcacagg | gaaaggagta | tgtcttcgtg | gcgaactcag | 780 |
| acaacttggg | tgctatagtt | gacatcaaga | tactaaacca | cctgatcact | aaccagaatg | 840 |
| agtactgcat | ggaagttact | ccaaaaaacat | tggctgatgt | taaaggtggt | accctcatct | 900 |
| catacgaagg | aagagtccag | ctcttggaga | ttgcccaagt | ccctgatgag | catgtgaatg | 960 |
| aattcaagtc | gattgagaag | ttcaagatat | ttaacaccaa | caacctgtgg | gtgaacttga | 1020 |
| aggcgatcaa | gaggcttgta | gatgctgaag | cacttaagat | ggaaatcatt | cccaacccta | 1080 |
| aggaagttga | tggcgtgaaa | gtcctgcagc | tagaaaccgc | agctggagca | gcgatcaggt | 1140 |
| tctttgagaa | ggcaatcggc | atcaacgttc | cccgctcaag | gtttctgccc | gtgaaggcta | 1200 |
| catctgattt | gttgcttgtg | cagtctgatc | tctatacctt | ggtcgatggc | tacgtcatcc | 1260 |
| gcaacccagc | cagagtgaag | ccatcgaacc | cttcaattga | gcttggtcct | gagttcaaaa | 1320 |
| aggttgccaa | cttccttgcc | cgtttcaaga | cgatccccag | catcgttgag | ctcgacagct | 1380 |
| tgaaggtctc | tggtgatgtc | tcgtttggct | ctggagtcgt | gctcgagggc | aacgtgacca | 1440 |
| tcgcagccaa | ggctggagtc | aagttggaga | tcccagacgg | agctgtgctg | gagaacaagg | 1500 |
| acatcaacgg | cccggaggat | ctttgagcgc | cgcccgccgc | cgttgccagt | tgcattccca | 1560 |
| gaaaccttcc | ggtcctcctt | cgttgagtta | accgtcctgt | aattttcgtg | tgcattctgc | 1620 |
| tggggtgttg | tcctgggata | gcccccttac | ataataattg | taatcccctc | tgtgctgttc | 1680 |
| atctacactt | gttcttcctg | ggcgtgccag | ggacgtaaaa | tttcttttgg | ttatatgatg | 1740 |
| cccatagttt | tcacatgcct | aaatttgttt | cttctttcgc | cctgctgggc | cgtaagagtt | 1800 |
| gcttttttgct | ggaa | | | | | 1814 |

<210> SEQ ID NO 12
<211> LENGTH: 473

```
<212> TYPE: PRT
<213> ORGANISM: Triticum aestivum

<400> SEQUENCE: 12

Met Ala Ala Ala Val Ala Ala Asp Ser Lys Ile Asp Gly Leu Arg
 1               5                  10                  15

Asp Ala Val Ala Lys Leu Gly Glu Ile Ser Glu Asn Glu Lys Ala Gly
                20                  25                  30

Phe Ile Ser Leu Val Ser Arg Tyr Leu Ser Gly Ala Glu Gln Ile
            35                  40                  45

Glu Trp Ser Lys Ile Gln Thr Pro Thr Asp Val Val Pro Tyr
     50                  55                  60

Asp Thr Leu Ala Pro Pro Glu Asp Leu Asp Ala Met Lys Ala Leu
 65              70                  75                  80

Leu Asp Lys Leu Val Val Leu Lys Leu Asn Gly Gly Leu Gly Thr Thr
                85                  90                  95

Met Gly Cys Thr Gly Pro Lys Ser Val Ile Glu Val Arg Asn Gly Phe
            100                 105                 110

Thr Phe Leu Asp Leu Ile Val Ile Gln Ile Glu Ser Leu Asn Lys Lys
        115                 120                 125

Tyr Gly Cys Ser Val Pro Leu Leu Met Asn Ser Phe Asn Thr His
        130                 135                 140

Asp Asp Thr Gln Lys Ile Val Glu Lys Tyr Ser Asn Ser Asn Ile Glu
145                 150                 155                 160

Ile His Thr Phe Asn Gln Ser Gln Tyr Pro Arg Ile Val Thr Glu Asp
                165                 170                 175

Phe Leu Pro Leu Pro Ser Lys Gly Gln Thr Gly Lys Asp Gly Trp Tyr
            180                 185                 190

Pro Pro Gly His Gly Asp Val Phe Pro Ser Leu Asn Asn Ser Gly Lys
        195                 200                 205

Leu Asp Thr Leu Leu Ser Gln Gly Lys Glu Tyr Val Phe Val Ala Asn
        210                 215                 220

Ser Asp Asn Leu Gly Ala Ile Val Asp Ile Lys Ile Leu Asn His Leu
225                 230                 235                 240

Ile Thr Asn Gln Asn Glu Tyr Cys Met Glu Val Thr Pro Lys Thr Leu
                245                 250                 255

Ala Asp Val Lys Gly Gly Thr Leu Ile Ser Tyr Glu Gly Arg Val Gln
            260                 265                 270

Leu Leu Glu Ile Ala Gln Val Pro Asp Glu His Val Asn Glu Phe Lys
        275                 280                 285

Ser Ile Glu Lys Phe Lys Ile Phe Asn Thr Asn Asn Leu Trp Val Asn
290                 295                 300

Leu Lys Ala Ile Lys Arg Leu Val Asp Ala Glu Ala Leu Lys Met Glu
305                 310                 315                 320

Ile Ile Pro Asn Pro Lys Glu Val Asp Gly Val Lys Val Leu Gln Leu
                325                 330                 335

Glu Thr Ala Ala Gly Ala Ala Ile Arg Phe Phe Glu Lys Ala Ile Gly
            340                 345                 350

Ile Asn Val Pro Arg Ser Arg Phe Leu Pro Val Lys Ala Thr Ser Asp
        355                 360                 365

Leu Leu Leu Val Gln Ser Asp Leu Tyr Thr Leu Val Asp Gly Tyr Val
        370                 375                 380

Ile Arg Asn Pro Ala Arg Val Lys Pro Ser Asn Pro Ser Ile Glu Leu
385                 390                 395                 400
```

-continued

```
Gly Pro Glu Phe Lys Lys Val Ala Asn Phe Leu Ala Arg Phe Lys Thr
            405                 410                 415
Ile Pro Ser Ile Val Glu Leu Asp Ser Leu Lys Val Ser Gly Asp Val
            420                 425                 430
Ser Phe Gly Ser Gly Val Val Leu Glu Gly Asn Val Thr Ile Ala Ala
            435                 440                 445
Lys Ala Gly Val Lys Leu Glu Ile Pro Asp Gly Ala Val Leu Glu Asn
            450                 455                 460
Lys Asp Ile Asn Gly Pro Glu Asp Leu
465                 470

<210> SEQ ID NO 13
<211> LENGTH: 473
<212> TYPE: PRT
<213> ORGANISM: Hordeum vulgare

<400> SEQUENCE: 13

Met Ala Ala Ala Val Ala Ala Asp Ser Lys Ile Asp Gly Leu Arg
  1               5                  10                  15
Asp Ala Val Ala Lys Leu Gly Glu Ile Ser Glu Asn Glu Lys Ala Gly
             20                  25                  30
Phe Ile Ser Leu Val Ser Arg Tyr Leu Ser Gly Glu Ala Glu Gln Ile
         35                  40                  45
Glu Trp Ser Lys Ile Gln Thr Pro Thr Asp Glu Val Val Pro Tyr
     50                  55                  60
Asp Thr Leu Ala Pro Pro Glu Asp Leu Asp Ala Met Lys Ala Leu
 65                  70                  75                  80
Leu Asp Lys Leu Val Val Leu Lys Leu Asn Gly Gly Leu Gly Thr Thr
                 85                  90                  95
Met Gly Cys Thr Gly Pro Lys Ser Val Ile Glu Val Arg Asn Gly Phe
            100                 105                 110
Thr Phe Leu Asp Leu Ile Val Ile Gln Ile Glu Ser Leu Asn Lys Lys
         115                 120                 125
Tyr Gly Cys Ser Val Pro Leu Leu Leu Met Asn Ser Phe Asn Thr His
     130                 135                 140
Asp Asp Thr Gln Lys Ile Val Glu Lys Tyr Ser Asn Ser Asn Ile Glu
145                 150                 155                 160
Ile His Thr Phe Asn Gln Ser Gln Tyr Pro Arg Ile Val Thr Glu Asp
                165                 170                 175
Phe Leu Pro Leu Pro Ser Lys Gly Gln Thr Gly Lys Asp Gly Trp Tyr
            180                 185                 190
Pro Pro Gly His Gly Asp Val Phe Pro Ser Leu Asn Asn Ser Gly Lys
         195                 200                 205
Leu Asp Thr Leu Leu Ser Gln Gly Lys Glu Tyr Val Phe Val Ala Asn
     210                 215                 220
Ser Asp Asn Leu Gly Ala Ile Val Asp Ile Lys Ile Leu Asn His Leu
225                 230                 235                 240
Ile His Asn Gln Asn Glu Tyr Cys Met Glu Val Thr Pro Lys Thr Leu
                245                 250                 255
Ala Asp Val Lys Gly Gly Thr Leu Ile Ser Tyr Glu Gly Arg Val Gln
            260                 265                 270
Leu Leu Glu Ile Ala Gln Val Pro Asp Glu His Val Asp Glu Phe Lys
         275                 280                 285
Ser Ile Glu Lys Phe Lys Ile Phe Asn Thr Asn Asn Leu Trp Val Asn
```

-continued

```
                        290                 295                 300
Leu Lys Ala Ile Lys Arg Leu Val Asp Ala Glu Ala Leu Lys Met Glu
305                 310                 315                 320

Ile Ile Pro Asn Pro Lys Glu Val Asp Gly Val Lys Val Leu Gln Leu
                325                 330                 335

Glu Thr Ala Ala Gly Ala Ala Ile Arg Phe Phe Glu Lys Ala Ile Gly
                340                 345                 350

Ile Asn Val Pro Arg Ser Arg Phe Leu Pro Val Lys Ala Thr Ser Asp
                355                 360                 365

Leu Leu Leu Val Gln Ser Asp Leu Tyr Thr Leu Val Asp Gly Tyr Val
    370                 375                 380

Ile Arg Asn Pro Ala Arg Val Lys Pro Ser Asn Pro Ser Ile Glu Leu
385                 390                 395                 400

Gly Pro Glu Phe Lys Lys Val Ala Asn Phe Leu Ala Arg Phe Lys Ser
                405                 410                 415

Ile Pro Ser Ile Val Glu Leu Asp Ser Leu Lys Val Ser Gly Asp Val
                420                 425                 430

Ser Phe Gly Ser Gly Val Val Leu Lys Gly Asn Val Thr Ile Ala Ala
            435                 440                 445

Lys Ala Gly Val Lys Leu Glu Ile Pro Asp Gly Ala Val Leu Glu Asn
    450                 455                 460

Lys Asp Ile Asn Gly Pro Glu Asp Ile
465                 470
```